US012702378B2

(12) United States Patent
Yang et al.

(10) Patent No.: US 12,702,378 B2
(45) Date of Patent: Aug. 11, 2026

(54) MEDICAL APPARATUS CART HAVING OPERATING CONSOLE WITH ROTATING HANDLE VIA WIRE TO ADJUST THE POSITION OF THE CONSOLE

(71) Applicant: GE Precision Healthcare LLC, Waukesha, WI (US)

(72) Inventors: Yalan Yang, Wuxi (CN); Mingze Yang, Wuxi (CN); Fenggui Huang, Wuxi (CN); Jie Wang, Wuxi (CN); Fangyu Huang, Wuxi (CN); Liang Wei, Wuxi (CN)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/886,847

(22) Filed: Sep. 16, 2024

(65) Prior Publication Data

US 2025/0099074 A1 Mar. 27, 2025

(30) Foreign Application Priority Data

Sep. 22, 2023 (CN) ......................... 202322591249.1

(51) Int. Cl.
*A61B 8/00* (2006.01)
*A61B 5/0245* (2006.01)
*A61B 50/13* (2016.01)
*A61B 50/24* (2016.01)

(52) U.S. Cl.
CPC .......... *A61B 8/4218* (2013.01); *A61B 5/0245* (2013.01); *A61B 8/4405* (2013.01); *A61B 50/13* (2016.02); *A61B 50/24* (2016.02)

(58) Field of Classification Search
CPC ... A61B 8/4218; A61B 5/0245; A61B 8/4405; A61B 50/13; A61B 50/24; A61B 5/333; A61B 8/4433; A61B 2560/0437; A61B 8/4411
See application file for complete search history.

(56) References Cited

U.S. PATENT DOCUMENTS

2022/0054107 A1 * 2/2022 Onodera .............. A61B 8/4405

FOREIGN PATENT DOCUMENTS

CN 113545799 A 10/2021

* cited by examiner

*Primary Examiner* — Serkan Akar

(57) ABSTRACT

A medical apparatus comprises: an operating console, a limiting mechanism, and a manual release mechanism. The limiting mechanism releases the limitation on movement of the operating console in a case where a pressing force is applied to the manual release mechanism. The manual release mechanism comprises: a handle, a conversion portion, and a base portion. The handle is provided with a first guide portion. The base portion is provided with a second guide portion that cooperates with the first guide portion. The handle moves linearly in a direction substantially perpendicular to the base portion under guidance of the first guide portion and the second guide portion in a case where the pressing force is applied to the handle. Thus, a smooth linear motion of the handle can be ensured to provide a good feeling of operation, helping to improve the user experience.

17 Claims, 6 Drawing Sheets

MEDICAL APPARATUS CART HAVING OPERATING CONSOLE WITH ROTATING HANDLE VIA WIRE TO ADJUST THE POSITION OF THE CONSOLE

CROSS-REFERENCE TO RELATED APPLICATION

This application claims priority to Chinese Patent Application No. 202322591249.1, which was file on Sep. 22, 2023 at the Chinese Patent Office. The entire contents of the above-listed application are incorporated by reference herein in their entirety.

TECHNICAL FIELD

Embodiments of the present application relate to the technical field of medical instruments, and in particular to a medical apparatus.

BACKGROUND

In the field of medical devices, a variety of medical apparatuses are included, which include, but are not limited to, ultrasound imaging apparatuses, electrocardiographs, and monitors. A medical apparatus comprises operating components for performing various operations. In addition, in order to facilitate movement, the medical apparatus is typically disposed or integrated in a cart. For example, the cart is provided with an operating console on which the medical apparatus may be disposed, or the operating components of the medical apparatus may be integrated in the operating console on the cart, through which the medical apparatus is manipulated.

When a corresponding medical operation is performed with the medical apparatus, the position of the operating console needs to be adjusted in order to facilitate the manipulation of the medical apparatus. For example, when a corresponding examination operation is performed with an ultrasound diagnostic apparatus, a user (such as a doctor) needs to hold an ultrasound probe and move it over an examination region of a subject under examination, while manipulating the ultrasound diagnostic apparatus and observing images on a display device. In this case, if the positing of the operating console of the ultrasound diagnostic apparatus cannot be adjusted with respect to the ultrasound diagnostic apparatus as a whole, there is a problem of difficulty in operation.

At present, the medical apparatus typically further includes a movement operation component for adjusting the position of the operating console. By the movement operation component, the position, for example, up-down position and/or horizontal position, of the operating console can be adjusted.

In some existing structures, the movement operation component includes a lifting portion that enables the operating console to move up and down and a rotating portion that enables the operating console to rotate in a horizontal plane. The lifting portion and the rotating portion are connected to the operating console. The movement operation component further includes a switch portion which is connected to the lifting portion and the rotating portion through wires, respectively. In a case where the position of the operating console needs to be adjusted, the user may cause the lifting portion and the rotating portion to act by operating the switch portion, so as to enable up-down movement and/or rotation in the horizontal plane of the operating console.

It should be noted that the above introduction of the background is only for the convenience of clearly and completely describing the technical solutions of the present application, and for the convenience of understanding for those skilled in the art.

SUMMARY

The inventor(s) found that among the existing movement operation components, some adopt a grip-type switch portion, similar to a brake structure of a bicycle handle, where a wire is directly connected to the switch portion to transmit an acting force, with the layout of the wire is more limited, and some adopt a press-type switch portion, where a pressing force acting on the switch component can be converted into a force in a direction intersecting a direction of the pressing force to stretch the wire. However, during one-handed operation, the switch portions may likely be stuck due to factors such as a change in a direction of the force or an uneven force, resulting in an adversely affected experience in the operation.

In view of at least one of the above technical problems, embodiments of the present application provide a medical apparatus.

According to the embodiments of the present application, there is provided a medical apparatus, comprising:

an operating console;

a limiting mechanism connected to the operating console, the limiting mechanism being capable of limiting movement of the operating console; and a manual release mechanism connected to the limiting mechanism through a wire, the limiting mechanism releasing the limitation on the movement of the operating console in a case where a pressing force is applied to the manual release mechanism, and the manual release mechanism comprising:

a handle receiving the pressing force;

a conversion portion connected to the handle and converting the pressing force into an acting force on the wire, a direction of the acting force intersecting a direction of the pressing force; and a base portion on which the handle and the conversion portion are mounted, wherein the handle is provided with a first guide portion, the base portion is provided with a second guide portion that cooperates with the first guide portion, and in a case where the pressing force is applied to the handle, the handle moves linearly in a direction substantially perpendicular to the base portion under guidance of the first guide portion and the second guide portion.

In one or some embodiments, a lever is connected to the end of the wire away from the manual release mechanism, the lever is connected to the limiting mechanism, and the limiting mechanism is driven by the lever to release the limitation on the movement of the operating console.

In one or some embodiments, a stroke of the wire is greater than a stroke of the handle.

In one or some embodiments, the conversion portion comprises:

a first connecting rod of which one end is disposed at the handle and is rotatable;

a sliding portion connected to the other end of the first connecting rod, the wire being fixed to the sliding portion; and a guide groove disposed at the base portion, an extension direction of the guide groove intersecting the direction of the pressing force, and in the case where the pressing force is applied to the handle, the sliding portion moving along the guide groove.

In one or some embodiments, the first connecting rod includes two rod portions, one end of each of the rod portions being disposed at the handle, and the sliding portion has a quadrangular structure, comprising:

a connecting portion of which both ends are respectively connected to the other ends of the two rod portions through idle wheels;

a locking portion arranged in parallel with the connecting portion, the wire being fixed to the locking portion; and a second connecting rod connected to corresponding end portions of the locking portion and the connecting portion.

In one or some embodiments, the conversion portion comprises:

a first idle wheel disposed at the handle, and a second idle wheel disposed at the base portion, the second idle wheel and the first idle wheel being disposed at different positions in an extension direction of the wire, the wire being disposed between the first idle wheel and the second idle wheel, an end portion of the wire being fixed to the base portion, and the first idle wheel and the second idle wheel pressing the wire in the case where the pressing force is applied to the handle.

In one or some embodiments, the number of the first idle wheels is two, the number of the second idle wheels is two, the two first idle wheels and the two second idle wheels are sequentially arranged at intervals, and the end portion of the wire fixed to the base portion is close to one of the two first idle wheels.

In one or some embodiments, the conversion portion comprises:

a rack disposed at the handle, and a gear disposed at the base portion and capable of being driven by the rack to rotate, the wire being fixed to the gear.

In one or some embodiments, an outer peripheral portion of the gear includes a toothed portion that meshes with the rack, and an extension portion to which the wire is fixed, and a distance of a fixed position of the wire from a rotation center of the gear is greater than a distance of the toothed portion of the gear from the rotation center.

In one or some embodiments, the wire is capable of transmitting a pulling force, and the conversion portion converts the pressing force into a stretching force on the wire; or, the wire is capable of transmitting a pushing force, and the conversion portion converts the pressing force into a pushing force on the wire.

In one or some embodiments, the medical apparatus comprises a gripping mechanism, comprising:

a gripping portion at which the manual release mechanism is disposed; and a front handle portion extending from an end portion of the gripping portion and connected to the operating console, the wire extending out of the manual release mechanism extending along and through the front handle portion.

In one or some embodiments, the manual release mechanism is disposed at the operating console.

In one or some embodiments, the limiting mechanism includes at least one of a lifting limiting mechanism and a rotating limiting mechanism, and in the case where the pressing force is applied to the manual release mechanism, the limiting mechanism releases the limitation on lifting and/or the movement of the operating console.

In one or some embodiments, the first guide portion is a protruding portion, the second guide portion is a recessed portion, and extension directions of the protruding portion and the recessed portion are parallel to the direction of the pressing force, or the first guide portion is a recessed portion, the second guide portion is a protruding portion, and extending directions of the protruding portion and the recessed portion are parallel to the direction of the pressing force.

In one or some embodiments, the medical apparatus comprises at least one of an ultrasound imaging apparatus, an electrocardiograph, and a monitor.

One of the beneficial effects of the embodiments of the present application is that: in the case where the pressing force is applied to the handle, the handle moves linearly in a direction substantially perpendicular to the base portion under guidance of the first guide portion and the second guide portion, which can ensure a smooth linear motion of the handle to provide a good feeling of operation, helping to improve the user experience.

With reference to the following description and drawings, specific implementations of the embodiments of the present application are disclosed in detail, and the way in which the principles of the embodiments of the present application can be employed are illustrated. It should be understood that the implementations of the present application are therefore not limited in scope. Within the scope of the spirit and clauses of the appended claims, the implementations of the present application include many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and a person of ordinary skill in the art may obtain other implementations according to the drawings without involving inventive skill. In the drawings.

DETAILED DESCRIPTION

The foregoing and other features of the embodiments of the present application will become apparent from the following description and with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first" and "second" etc., are used to distinguish different elements, but do not represent a spatial arrangement or temporal order, etc., of these elements, and these elements should not be limited by these terms. The term "and/or" includes any and all combinations of one or more associated listed terms. The terms "comprise", "include", "have", etc., refer to the presence of described features, elements, components, or assemblies, but do not exclude the presence or addition of one or more other features, elements, components, or assemblies.

In the embodiments of the present application, the singular forms "a" and "the", etc., include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "on the basis of" should be construed as "at least in part on the basis of . . . ", unless otherwise specified in the context.

In the description of the present application, it should be noted that, unless otherwise expressly defined and specified, the terms "join" and "connect" are to be understood in a broad sense, for example, as a fixed, detachable or integral connection; as a mechanical or electrical connection; as a direct connection or an indirect connection by means of an intermediate medium; the specific meaning of the above terms in the context of the present application will be understood by those of ordinary skill in the art in the specific context.

The features described and/or illustrated for one implementation may be used in one or more other implementations in the same or similar manner, be combined with features in other implementations, or replace features in other implementations. The term "include/comprise" when used herein refers to the presence of features, integrated components, steps, or assemblies, but does not preclude the presence or addition of one or more other features, integrated components, steps, or assemblies.

The embodiments of the present application are specifically described below.

Figure 1:
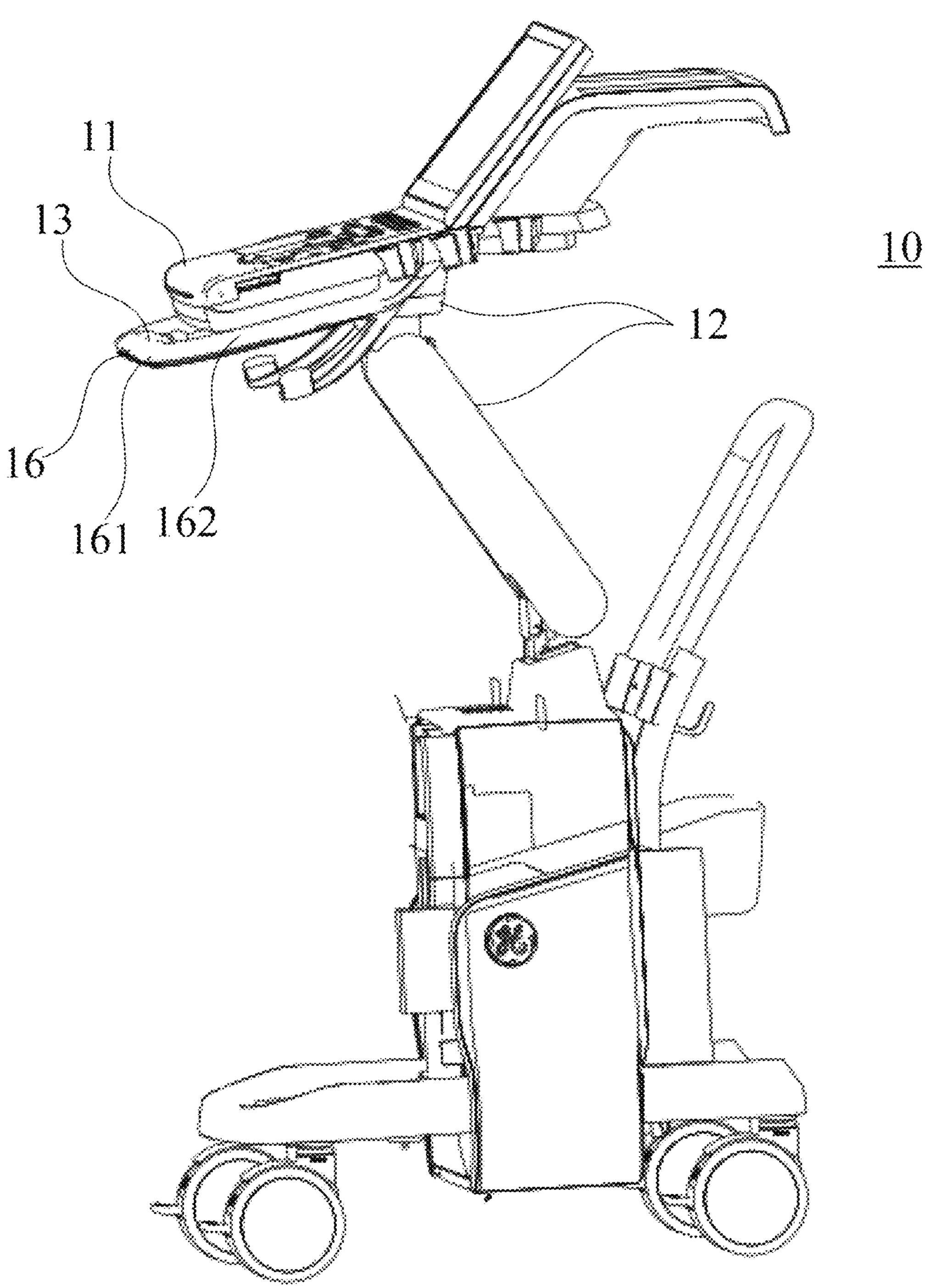
FIG. 1 is a schematic diagram of the structure of a medical apparatus of an embodiment of the present application.

Embodiments of the present application provide a medical apparatus. FIG. 1 is a schematic diagram of the structure of a medical apparatus of an embodiment of the present application.

As shown in FIG. 1, a medical apparatus 10 includes: an operating console 11, a limiting mechanism 12, and a manual release mechanism 13. The limiting mechanism 12 is connected to the operating console 11, and the limiting mechanism can limit movement of the operating console 11.

Figure 2:
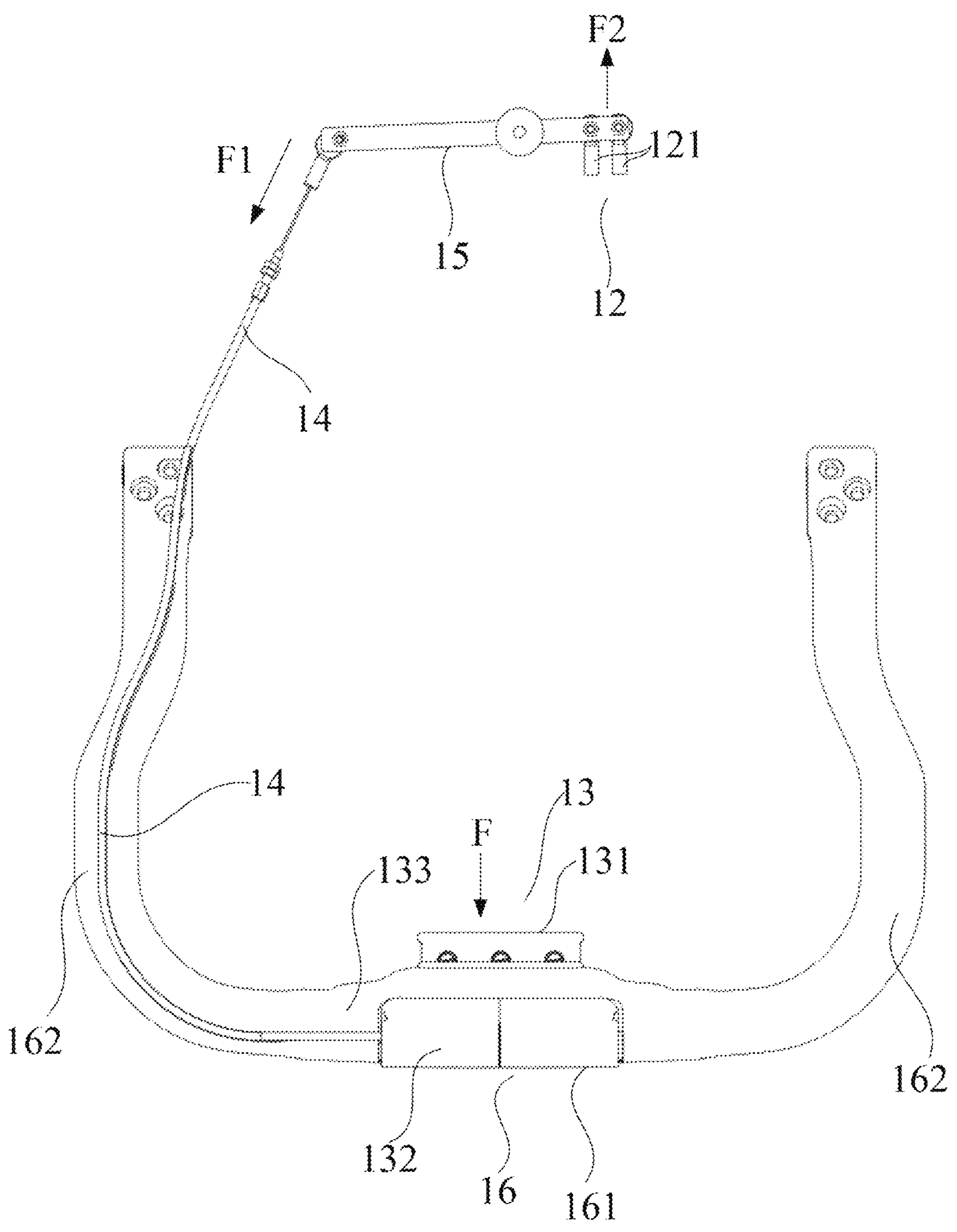
FIG. 2 is a schematic diagram of an embodiment of the present application including a manual release mechanism.

FIG. 2 is a schematic diagram of an embodiment of the present application including a manual release mechanism.

As shown in FIG. 2, the manual release mechanism 13 is connected to the limiting mechanism 12 through a wire 14. In a case where a pressing force is applied to the manual release mechanism 13, the limiting mechanism 12 releases the limitation on the movement of the operating console 11.

It should be noted that, FIG. 2 only schematically shows a joint portion 121 of the limiting mechanism 12 connected to the wire 14, but the limiting mechanism 12 further includes a limiting structure, such as an air spring, a rotating mechanism engaged via a hook, which cooperates with the joint portion 121 and is connected to the operating console. The action of the joint portion 121 driven by the wire 14 can cause the limiting structure to release the limitation on the movement of the operating console. Reference may be made to the related art, which will not be introduced again herein.

As shown in FIG. 2, the manual release mechanism 13 includes a handle 131, a conversion portion 132, and a base portion 133. The handle 131 and the conversion portion 132 are mounted on the base portion 133. The handle 131 receives a pressing force F. The conversion portion 132 is connected to the handle 131 and converts the pressing force F into an acting force on the wire 14. A direction of the acting force intersects a direction of the pressing force F, where intersecting means that two directions are not parallel or do not coincide. For example, the acting force on the wire 14 and the pressing force F may be substantially perpendicular or at other angles, which is not limited in the present application.

Figure 3:
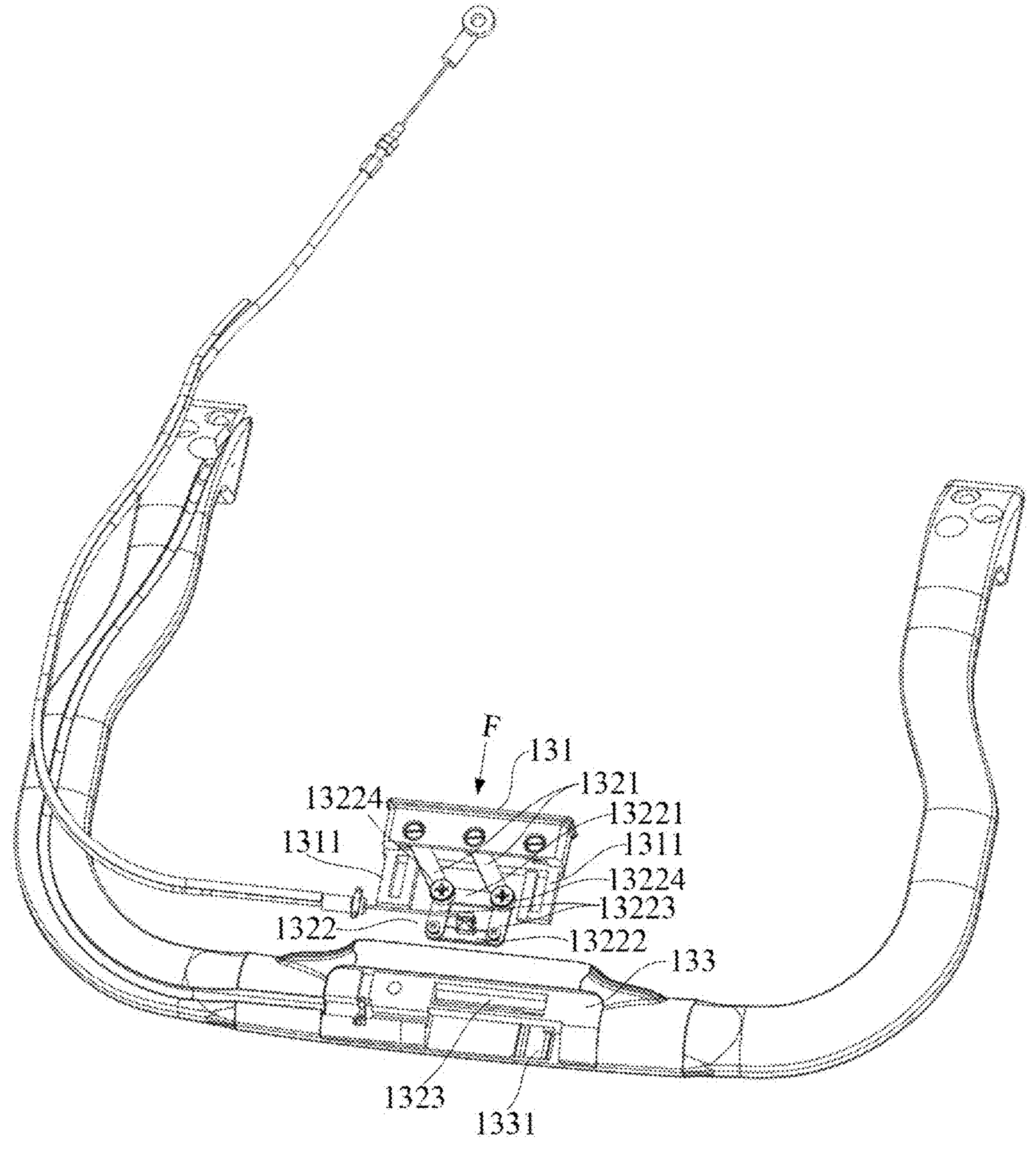
FIG. 3 is a schematic diagram of a manual release mechanism of an embodiment of the present application.

FIG. 3 is a schematic diagram of a manual release mechanism of an embodiment of the present application, showing a situation in which a handle and a conversion portion are in an unassembled state with a base portion.

As shown in FIG. 3, the handle 131 is provided with a first guide portion 1311, and the base portion 133 is provided with a second guide portion 1331 cooperating with the first guide portion 1311. In a case where the pressing force is applied to the handle 131, the handle 131 moves linearly in a direction substantially perpendicular to the base portion 133 under guidance of the first guide portion 1311 and the second guide portion 1331. As shown in FIG. 3, the base portion 133 is in the shape of an elongated strip extending in a direction substantially perpendicular to the direction of the pressing force F, and the handle 131 moves linearly in the direction substantially perpendicular to the base portion 133, which can be understood as the moving direction of the handle 131 being substantially perpendicular to the extension direction of the base portion 133. It can be understood that "substantially" means tolerance for errors above or below an included angle of 90° due to factors well-known in the art such as manufacturing precision, assembly precision, etc.

According to the embodiments described above, in the case where the pressing force is applied to the handle, the handle moves linearly in the direction substantially perpendicular to the base portion under guidance of the first guide portion and the second guide portion. Thus, a smooth linear motion of the handle can be ensured to provide a good feeling of operation, helping to improve the user experience. In particular, when the user holds the handle with one hand, the presence of the guide portions can ensure that the motion of the handle is not stuck due to an uneven holding force applied at a holding position, thereby ensuring that the user holding and pressing the handle with one hand can still cause the manual release structure serving as the switch portion to release the limitation on the operating console, enabling the user to perform operations such as lifting and/or rotation on the operating console.

As shown in FIG. 2, in one or more embodiments, a lever 15 is connected to the end of the wire 14 away from the manual release mechanism 13. The lever 15 is connected to the limiting mechanism 12, and the limiting mechanism 12 is driven by the lever 15 to release the limitation on the movement of the operating console.

Thus, by providing the lever 15, the required operating force can be reduced, and the ease of operation with one hand can be further ensured, improving the feeling of operation.

In one or more embodiments, a stroke of the wire is greater than a stroke of the handle. That is, in the process of pressing the handle to release the limitation on the movement of the operating console by the limiting mechanism, the amount of displacement of the handle is less than the amount of displacement of the wire. Thus, the user can release the limitation on the movement of the operating console without the need for a large pressing stroke, and the feeling of operation can be further improved.

Next, the specific structure of the manual release mechanism will be exemplarily described.

As shown in FIG. 3, in one or more embodiments, the conversion portion 132 includes a first connecting rod 1321, a sliding portion 1322, and a guide groove 1323. One end of the first connecting rod 1321 is disposed at the handle 131 and is rotatable, and the sliding portion 1322 is connected to the other end of the first connecting rod 1321. The wire 14 is fixed to the sliding portion 1322. The guide groove 1323 is disposed at the base portion 133, and an extension direction of the guide groove 1323 intersects the direction of the pressing force F.

Thus, when the handle 131 is pressed, the first connecting rod 1321 and the sliding portion 1322 can rotate together relative to the handle 131, such that the sliding portion 1322 slides along the guide groove 1323, thereby providing an acting force to the wire 14, and the acting force on the wire 14 intersects the direction of the pressing force F. Thus, the conversion of the direction of the force can be realized, and the layout of the wire will not be limited.

In the embodiments of the present application, a state where the handle 131 and the conversion portion 132 are mounted on the base portion 133 and the handle 131 is not subjected to the pressing force F is referred to as a natural state of the handle 131. In this natural state, the first connecting rod 1321 is inclined relative to the pressing force F, as shown in FIG. 3, in which case the stroke of the wire can be greater than the stroke of the handle.

For example, assuming that the length of the first connecting rod 1321 is 2 L, if the included angle between the first connecting rod 1321 and the pressing force F is 30 degrees in the natural state, and if the included angle between the first connecting 1321 and the pressing force F is 45 degrees in a release state (a state where pressing of the handle 131 means to release the limitation on the movement of the operating console is referred to as a release state of the handle 131), then from the natural state to the release state, the stroke of the handle 131 is $(\sqrt{3}-\sqrt{2})$ L, and the stroke of the wire 14 is $(\sqrt{2}-1)$ L. It follows that the stroke of the handle 131 is less than the stroke of the wire 14.

It should be noted that the value of the angle is merely exemplarily described, and in the natural state and the released state, the angle between the first connecting rod 1321 and the pressing force F may have other values, which is not limited in the present application.

In one or more embodiments, as shown in FIG. 3, the first connecting rod 1321 may include two rod portions. One end of each of the rod portions is disposed at the handle 131. The sliding portion 1322 has a quadrangular structure, including a connecting portion 13221, a locking portion 13222, and a second connecting rod 13223. Both ends of the connecting portion 13221 are respectively connected to the other ends of the two rod portions through idle wheels 13224. The locking portion 13222 is arranged in parallel with the connecting portion 13221. The wire 14 is fixed to the locking portion 13222. The second connecting rod 13223 is connected to corresponding end portions of the locking portion 13222 and the connecting portion 13221.

Thus, when the handle 131 is pressed, the first connecting rod 1321 and the idle wheels 13224 can rotate together relative to the handle 131, such that the idle wheels 13224 slide along the guide groove 1323, and the connecting portion 13221 and the locking portion 13222 move accordingly, thereby providing an acting force to the wire 14. Thus, the conversion of the direction of the force can be realized, and the layout of the wire will not be limited.

In one or more embodiments, the first connecting rod 1321 may be movably mounted on the handle 131 by a stop screw, but the present application is not limited thereto, as long as the first connecting rod 1321 is rotatable relative to the handle 131.

The form in which the wire 14 is fixed to the sliding portion 1322 or the locking portion 13222 is not limited in the embodiments of the present application. For example, as shown in FIG. 3, the locking portion 13222 may include a rod with both ends connected to the second connecting rod 13223, and a locking component disposed at the rod. The locking component includes a ball disposed at the end of the wire 14 and a lock fixed to the rod, and the ball is assembled to the lock. However, the present application is not limited thereto, and the wire 14 may also be otherwise fixed to the sliding portion 1322 in other ways.

In the embodiments of the present application, the idle wheels 13224 may be disposed at the guide groove 1323 and slide along the guide groove 1323. In this case, in the process of pressing the handle 131 to cause the sliding portion 1322 to slide, the wire 14 fixed to the sliding portion 1322 (the locking portion 13222) always moves in the direction substantially perpendicular to the pressing force F. Thus, it can ensure that the direction of the acting force on the wire 14 on the side at which the wire 14 extends out of the base portion 133 always remains unchanged, and can ensure the reliability of operation.

In one or more embodiments, the first guide portion 1311 is a protruding portion, the second guide portion 1331 is a recessed portion, and extension directions of the first guide portion 1311 and the second guide portion 1331 are parallel to the direction of the pressing force F. Thus, in the case where the pressing force F is applied to the handle 131, the handle 131 can move linearly in the direction substantially perpendicular to the base portion 133 under guidance of the first guide portion 1311 and the second guide portion 1331.

For example, FIG. 3 shows that the first guide portion 1311 is in the shape of an elongated plate as a protruding portion, and the second guide portion 1331 is a groove as a recessed portion, but the present application is not limited thereto, and the first guide portion 1311 and the second guide portion 1331 may also have other shapes.

In the embodiments of the present application, as shown in FIG. 3, a through hole may be provided in the middle of the elongated plate of the first guide portion 1311. Thus, the handle 131 can be more easily pressed into the base portion 133.

In addition, the first guide portion may also be a recessed portion, and correspondingly, the second guide portion may be a protruding portion, and extension directions of the protruding portion and the recessed portion are parallel to the direction of the pressing force. Thus, in the case where the pressing force F is applied to the handle 131, the handle 131 can also move linearly in the direction substantially perpendicular to the base portion 133 under guidance of the first guide portion and the second guide portion.

In one or more embodiments, as shown in FIG. 3, there are two first guide portions 1311 respectively located at two ends of the handle 131. However, the present application is not limited thereto, and the number of the first guide portions 1311 may also be one, which for example may be disposed in the middle of the handle 131, or may be disposed at other positions of the handle 131. Furthermore, the number of the first guide portions 1311 may also be a plurality more than two, and the plurality of first guide portions 1311 may be arranged at equal or unequal intervals on the handle 131, which is not limited in the present application. Additionally, two first guide portions 1311 may also be arranged at other positions of the handle 131, for example, the position near the middle of the handle, which is not limited in the present application. Moreover, a corresponding number of second guide portions are arranged at corresponding positions of the base portion, which will not be introduced again herein.

FIG. 3 is a schematic diagram of one implementation of the manual release mechanism of an embodiment of the present application, but the present application is not limited thereto, and the manual release mechanism may also have other structures.

Figure 4:
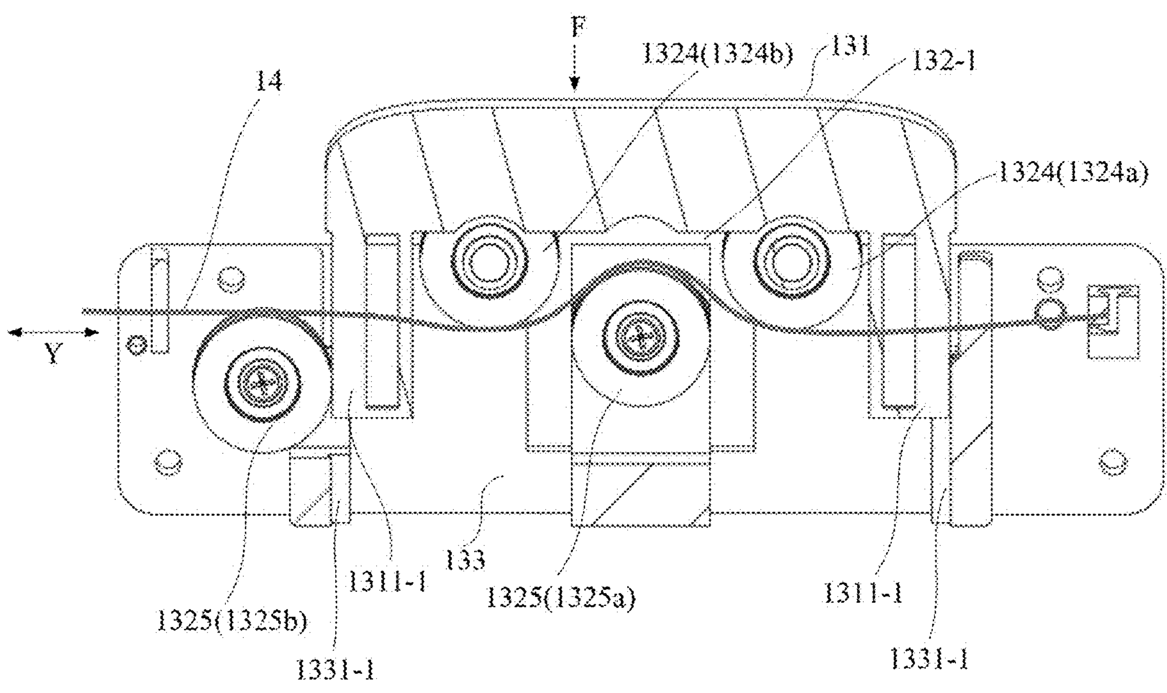
FIG. 4 is another schematic diagram of a manual release mechanism of an embodiment of the present application.
Figure 5:
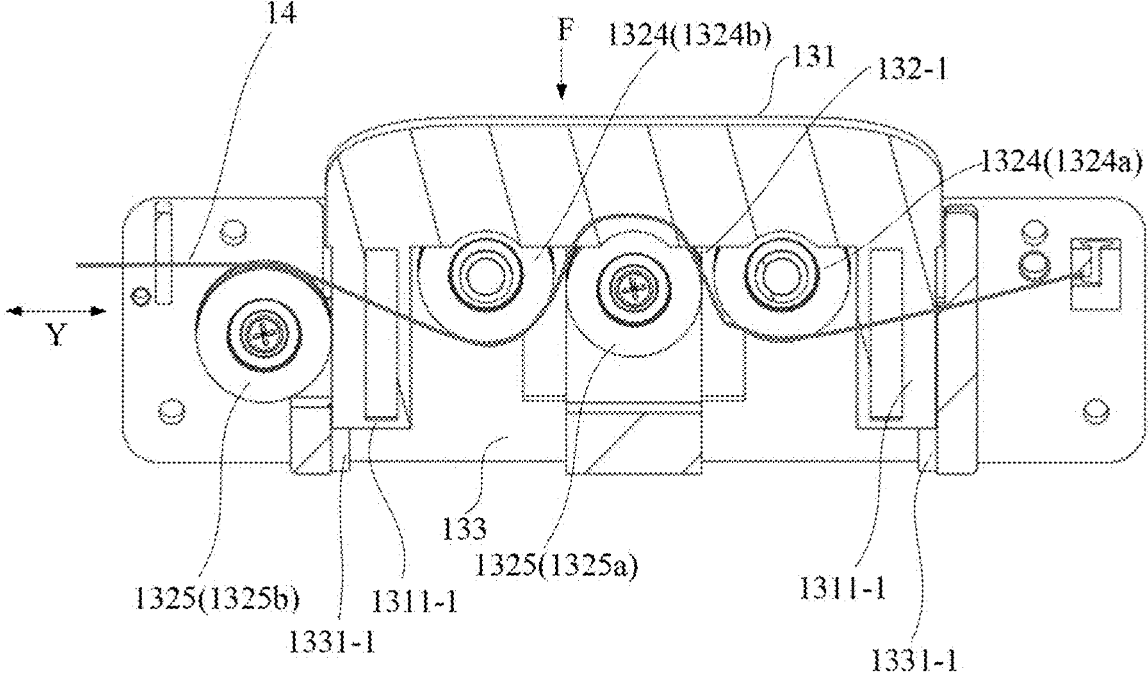
FIG. 5 is yet another schematic diagram of the manual release mechanism shown in FIG. 4.

For example, FIG. 4 is another schematic diagram of a manual release mechanism of an embodiment of the present application, showing another implementation of the manual release mechanism. FIG. 5 is yet another schematic diagram of the manual release mechanism shown in FIG. 4, showing a situation in which a handle is fully pressed into a base portion.

As shown in FIGS. 4 and 5, in one or more embodiments, a conversion portion 132-1 includes a first idle wheel 1324 and a second idle wheel 1325. The first idle wheel 1324 is disposed at the handle 131, and the second idle wheel 1325 is disposed at the base portion 133. The second idle wheel 1325 and the first idle wheel 1324 are disposed at different positions in an extension direction Y of the wire 14. The wire 14 is disposed between the first idle wheel 1324 and the second idle wheel 1325. An end portion of the wire 14 is fixed to the base portion 133. In the case where the pressing force is applied to the handle 131, the first idle wheel 1324 and the second idle wheel 1325 press the wire.

Thus, when the handle 131 is pressed, the first idle wheel 1324 and the second idle wheel 1325 press the wire 14 which bends under the pressure of the handle 131, thereby providing an acting force to the wire 14. The acting force on the wire 14 intersects the direction of the pressing force F. Thus, the conversion of the direction of the force can be realized, and the layout of the wire will not be limited.

In the embodiments of the present application, the ratio of the stroke of the wire to the stroke of the handle is a multiple of the number of the first idle wheels 1324 in a structure in which the conversion portion is implemented by the idle wheels. For example, when the number of the first idle wheels 1324 is one, the stroke of the wire may be twice the stroke of the handle, and when the number of the first idle wheels 1324 is two as shown in FIGS. 4 and 5, the stroke of the wire may be four times the stroke of the handle, thus enabling the stroke of the wire to be greater than the stroke of the handle, thereby improving the feeling of operation.

As shown in FIGS. 4 and 5, in one or more embodiments, the number of the first idle wheels 1324 is two, and the number of the second idle wheels 1325 is two. The two first idle wheels 1324 and the two second idle wheels 1325 are sequentially arranged at intervals. An end portion of the wire 14 fixed to the base portion 133 is close to one of the two first idle wheels 1324.

As shown in FIGS. 4 and 5, starting from the end portion of the wire 14 fixed to the base portion 133, the first idle wheel **1324*a*, the second idle wheel 1325*a*, the first idle wheel 1324*b*, and the second idle wheel 1325*b* are sequentially provided. Thus, the wire 14 extends out of the base portion 133 passing the second idle wheel 1325*b* fixed to the base portion 133, which can ensure that the direction of the acting force on the wire 14 on the side at which the wire 14 extends out of the base portion 133** always remains unchanged, and ensure the reliability of operation.

FIGS. 4 and 5 show that the number of the first idle wheels 1324 is two, but the present application is not limited thereto. For example, there may be one first idle wheel 1324. For example, only the first idle wheel **1324*b* is retained without the first idle wheel 1324*a*, or vice versa. Alternatively, the number of the first idle wheels 1324 may be three or more, and may be arranged as needed. Furthermore, the number and arrangement of the second idle wheels 1325** may be adaptively arranged according to the arrangement of the first idle wheels.

FIGS. 4 and 5 show that the number of the second idle wheels 1325 is two, but the present application is not limited thereto. For example, there may be one second idle wheel 1325. For example, only the second idle wheel **1325*a* is retained without the second idle wheel 1325*b*, or vice versa. Alternatively, the number of the second idle wheels 1325 may be three or more, and may be arranged as needed. Furthermore, the number and arrangement of the first idle wheels 1324** may be adaptively arranged according to the arrangement of the second idle wheels.

As shown in FIGS. 4 and 5, in one or more embodiments, a first guide portion 1311-1 is a protruding portion, a second guide portion 1331-1 is a recessed portion, and extension directions of the first guide portion 1311-1 and the second guide portion 1331-1 are parallel to the direction of the pressing force F. Thus, in the case where the pressing force F is applied to the handle 131, the handle 131 can move linearly in the direction substantially perpendicular to the base portion 133 under guidance of the first guide portion 1311-1 and the second guide portion 1331-1.

In addition, for the first guide portion 1311-1 and the second guide portion 1331-1, reference may be made to the above description for the first guide portion 1311 and the second guide portion 1331, which will not be introduced again here.

Figure 6:
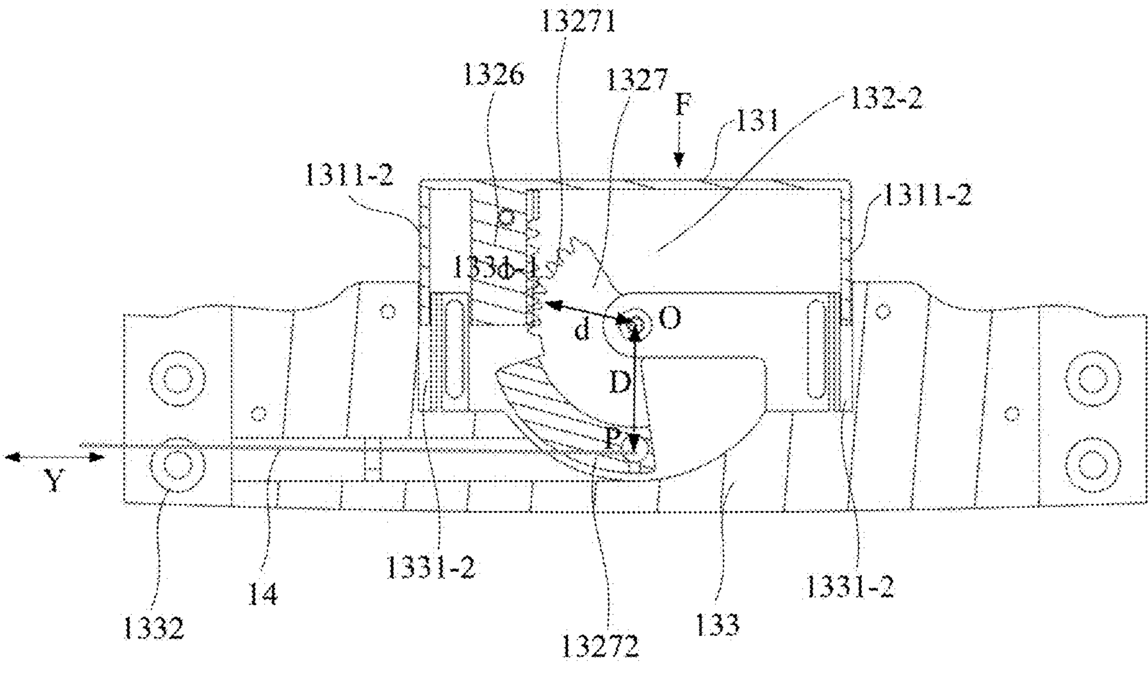
FIG. 6 is yet another schematic diagram of a manual release mechanism of an embodiment of the present application.

FIG. 6 is yet another schematic diagram of a manual release mechanism of an embodiment of the present application, showing yet another implementation of a manual release mechanism.

As shown in FIG. 6, in one or more embodiments, a conversion portion 132-2 includes a rack 1326 and a gear 1327. The rack 1326 is disposed at the handle 131. The gear

1327 is disposed at the base portion 133 and can be driven by the rack 1326 to rotate. The wire 14 is fixed to the gear 1327.

Thus, when the handle 131 is pressed, the gear 1327 is driven by the rack 1326 to rotate, thereby providing an acting force to the wire 14 fixed to the gear 1327. The acting force on the wire 14 intersects the direction of the pressing force F. Thus, the conversion of the direction of the force can be realized, and the layout of the wire will not be limited.

As shown in FIG. 6, in one or more embodiments, an outer peripheral portion of the gear 1327 includes a toothed portion 13271 and an extension portion 13272. The toothed portion 13271 meshes with the rack 1326. The wire 14 is fixed to the extension portion 13272, and a distance D of a fixed position P of the wire 14 from a rotation center O of the gear 1327 is greater than a distance d of the toothed portion 13271 of the gear 1327 from the rotation center O.

Thus, in a structure in which the conversion portion is implemented by the gear, since the distance of the fixed position P of the wire 14 with respect to the rotation center O is greater than the distance between the rotation center and the toothed portion 13271, enabling the stroke of the wire to be greater than the stroke of the handle in the process of pressing the handle 131, thereby improving the feeling of operation.

The specific dimensions of the distance D and the distance d are not limited in the embodiments of the present application, as long as they can enable the stroke of the wire to be greater than the stroke of the handle in the process of pressing the handle 131.

As shown in FIG. 6, in one or more embodiments, the base portion 133 may be provided with a guide portion 1332 thereon through which the wire 14 is led out to the base portion 133. Thus, the wire 14 can extend out of the base portion 133 by the guide portion 1332 fixed to the base portion 133, which can ensure that the direction of the acting force on the wire 14 on the side at which the wire 14 extends out of the base portion 133 always remains unchanged, for example, always in the Y direction, and can ensure the reliability of operation.

As shown in FIG. 6, in one or more embodiments, a first guide portion 1311-2 is a protruding portion, a second guide portion 1331-2 is a recessed portion, and extension directions of the first guide portion 1311-2 and the second guide portion 1331-2 are parallel to the direction of the pressing force F. Thus, in the case where the pressing force F is applied to the handle 131, the handle 131 can move linearly in the direction substantially perpendicular to the base portion 133 under guidance of the first guide portion 1312-1 and the second guide portion 1332-1.

In addition, for the first guide portion 1311-2 and the second guide portion 1331-2, reference may be made to the above description for the first guide portion 1311 and the second guide portion 1331, which will not be introduced again here.

In one or more embodiments, the wire 14 is capable of transmitting a pulling force, and the conversion portion (132, 132-1, 132-2) converts the pressing force F into a stretching force on the wire 14.

As shown in FIG. 2, under the pulling of the wire 14, the wire 14 applies a pulling force F1 to the lever, and the lever 15 converts the pulling force F1 into a pulling force F2 to cause the limiting mechanism to act. Thus, the wire 14 is pulled by pressing the handle 131, thereby releasing the limitation on the movement of the operating console.

In the embodiments of the present application, the wire 14 may be, for example, a Bowden wire, but the present application is not limited thereto. The wire 14 may be another type of wire as long as it can transmit a pulling force.

However, the present application is not limited thereto. For example, the wire may also be a wire that can transmit a pushing force, and the conversion portion converts the pressing force F into a pushing force on the wire. Thus, the wire can be pushed by pressing the handle 131, thereby releasing the limitation on the movement of the operating console. The wire which transmits a pushing force may be, for example, a hydraulic wire, such as an oil based hydraulic wire, but the present application is not limited thereto, as long as a pushing force can be transmitted.

Figure 7:
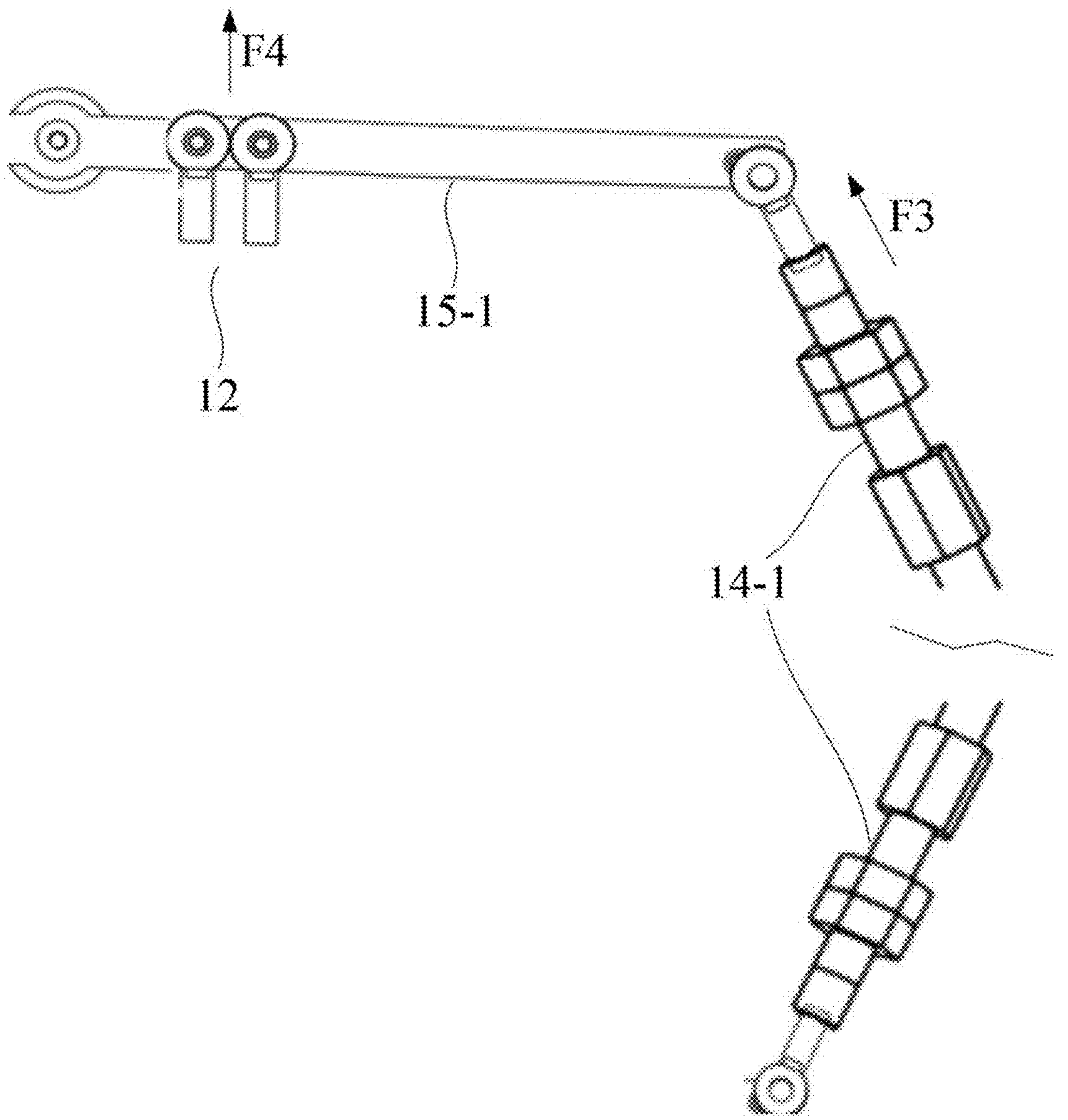
FIG. 7 is another schematic diagram of a wire of an embodiment of the present application.

FIG. 7 is another schematic diagram of a wire of an embodiment of the present application, showing an example of the structure of an oil based hydraulic wire.

As shown in FIG. 7, under the pushing of an oil based hydraulic wire 14-1, the oil based hydraulic wire 14-1 applies a pushing force F3 to a lever 15-1, and the lever 15-1 converts the pushing force F3 into a pushing force F4 to cause the limiting mechanism 12 to act. Thus, the oil based hydraulic wire 14-1 is pushed by pressing the handle, thereby releasing the limitation on the movement of the operating console.

In the embodiments of the present application, the oil based hydraulic wire 14-1 may include a ball joint, an oil cylinder rod, and an oil cylinder tube in sequence at both ends. Regarding the oil based hydraulic wire, reference may be made to the related art.

As shown in FIGS. 1 and 2, in one or some embodiments, the medical apparatus 10 may include a gripping mechanism 16, which includes a gripping portion 161 and a front handle portion 162. The manual release mechanism 13 may be disposed at the gripping portion 161. The front handle portion 162 extends from an end portion of the gripping portion 161 and is connected to the operating console 11. The wire 14 extending out of the manual release mechanism 13 extends along and through the front handle portion 162.

Thus, the user can complete the operation of releasing the operating console and moving the position of the operating console with one hand, which can improve convenience. Furthermore, the wire 14 can be received in the front handle portion 162, which can avoid interference between the wire and other components of the medical apparatus.

However, the present application is not limited thereto, and the manual release mechanism may also be disposed at other positions of the medical apparatus. For example, the manual release mechanism may be disposed at the operating console.

In one or some embodiments, the limiting mechanism 12 includes at least one of a lifting limiting mechanism and a rotating limiting mechanism. In the case where the pressing force is applied to the manual release mechanism, the limiting mechanism releases the limitation on the lifting and/or movement of the operating console.

For example, as shown in FIG. 2, the limiting mechanism 12 has two joint portions 121, one of which may be used for a lifting limiting mechanism, and the other may be used for a rotating limiting mechanism. Thus, the user may complete the release of the lifting limiting mechanism and the rotating limiting mechanism with one hand, thereby enabling the lifting operation and the rotating operation.

It can be understood that the lifting operation and the rotating operation may be implemented in any manner in the prior art. An exemplary description is provided below, but is not intended to be an exclusive limitation.

For example, in some examples, the medical apparatus may include at least one of a lifting portion and a rotating portion. The lifting portion and the rotating portion may be in a locked state, or the lifting portion and the rotating portion are constantly locked components. In the locked state, the position of the operating console is locked and cannot be moved. When the lifting portion and the rotating portion are released from the locked state by operating the manual release mechanism (the switch portion), the user may apply an acting force to the operating console to lift and/or rotate the operating console.

When the operation on the switch portion is removed, the lifting portion can automatically reset to be in the locked state again. For example, the lifting portion may be an air spring or the like, and automatically reset when the operation on the switch portion is removed. Alternatively, when the operation on the switch portion is removed, under the action of a damping component of the lifting portion, the lifting portion may be in a semi-locked state which means that in a case where the lifting portion is not subjected to an external force or the external force is less than a damping force of the damping component of the lifting portion, the lifting portion does not move, and thus the operating console does not lift. For example, when the operating console is at an appropriate height, the doctor stops a lifting force acting on the operating console, and the operating console stops lifting. When the operating console needs to be lifted again, the doctor may apply a lifting force to the operating console (a lifting table). In a case where an external force applied to the lifting portion exceeds the damping force of the damping component of the lifting portion, the lifting portion can move, and thus the operating console can be lifted. When the lifting portion moves to a position at a certain height, the lifting portion can be in the locked state again.

Similarly, when the operation on the switch portion is removed, the rotating portion can automatically reset to be in the locked state again, or to be in the semi-locked state under the action of a damping component of the rotating portion. The rotating portion may include, for example, engaging structures such as concave-convex cooperating structures, a hook, and a rotating mechanism that cooperates with the hook. When the engaging structures are in a mutually engaged state, the rotating portion is in the locked state and the operating console cannot be moved. When the rotating portion is released from the locked state by operating the switch component, the engaging structures are in a state where they are not engaged with each other, in which case the user can apply an action to the operating console (the rotating portion) to rotate the operating console. When the operation on the switch portion is removed, under the action of an automatic reset component, the rotating portion causes the engaging structures to be in the mutually engaged state so as to lock the rotating portion, or the rotating portion can be in the semi-locked state. When the user rotates the operating console such that an acting force applied to the rotating portion is greater than a damping force of the damping component of the rotating portion, the rotating portion can continue to rotate so that the operating console rotates, or otherwise the operating console does not rotate. Moreover, when the rotating portion rotates to a certain position, the engaging structures of the rotating portion can be in a mutually cooperating state again, so that the operating console cannot be rotated in the locked state.

In the embodiments of the present application, the medical apparatus 10 includes at least one of an ultrasound imaging apparatus, an electrocardiograph, and a monitor.

According to the above embodiments, in the case where the pressing force is applied to the handle 131, the handle moves linearly in the direction substantially perpendicular to the base portion 133 under guidance of the first guide portion (1311, 1311-1, 1311-2) and the second guide portion (1331, 1331-1, 1331-2), which can ensure a smooth linear motion of the handle 131 to provide a good feeling of operation, helping to improve the user experience.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

The present application is described above with reference to specific implementations. However, it should be clear to those skilled in the art that the foregoing description is merely illustrative and is not intended to limit the scope of protection of the present application. Various variations and modifications may be made by those skilled in the art according to the spirit and principle of the present application, and these variations and modifications also fall within the scope of the present application.

Preferred implementations of the present application are described above with reference to the accompanying drawings. Many features and advantages of the implementations are clear according to the detailed description, and therefore the appended claims are intended to cover all these features and advantages that fall within the true spirit and scope of these implementations. In addition, as many modifications and changes could be easily conceived of by those skilled in the art, the implementations of the present application are not limited to the illustrated and described precise structures and operations, but can encompass all appropriate modifications, changes, and equivalents that fall within the scope of the implementations.

The invention claimed is:

1. A medical apparatus, comprising:

an operating console of the medical apparatus;

a limiting mechanism connected to the operating console, the limiting mechanism being capable of limiting movement of the operating console; and a manual release mechanism connected to the limiting mechanism through a wire, the limiting mechanism releasing the limitation on the movement of the operating console based on a pressing force being applied to the manual release mechanism, and the manual release mechanism comprising:

a handle receiving the pressing force;

a conversion portion connected to the handle and converting the pressing force into an acting force on the wire, a direction of the acting force intersecting a direction of the pressing force; and a base portion on which the handle and the conversion portion are mounted, wherein the handle is provided with a first guide portion, the base portion is provided with a second guide portion that cooperates with the first guide portion, and in a case where the pressing force is applied to the handle, the handle moves linearly in a direction perpendicular to the base portion under guidance of the first guide portion and the second guide portion, wherein a lever is connected to the end of the wire away from the manual release mechanism, the lever is connected to the limiting mechanism, and the limiting mechanism is driven by the lever to release the limitation on the movement of the operating console, wherein a stroke of the wire is greater than a stroke of the handle, wherein the conversion portion comprises:

a first connecting rod of which one end is disposed at the handle and is rotatable;

a sliding portion connected to the other end of the first connecting rod, the wire being fixed to the sliding portion; and a guide groove disposed at the base portion, an extension direction of the guide groove intersecting the direction of the pressing force, and in the case where the pressing force is applied to the handle, the sliding portion moving along the guide groove.

2. The medical apparatus according to claim 1, wherein, the first connecting rod includes two rod portions, one end of each of the rod portions being disposed at the handle, and the sliding portion has a quadrangular structure, comprising:

a connecting portion of which both ends are respectively connected to the other ends of the two rod portions through idle wheels;

a locking portion arranged in parallel with the connecting portion, the wire being fixed to the locking portion; and a second connecting rod connected to corresponding end portions of the locking portion and the connecting portion.

3. The medical apparatus according to claim 1, wherein, the wire is capable of transmitting a pulling force, and the conversion portion converts the pressing force into a stretching force on the wire; or, the wire is capable of transmitting a pushing force, and the conversion portion converts the pressing force into a pushing force on the wire.

4. The medical apparatus according to claim 1, wherein, the medical apparatus comprises a gripping mechanism, comprising:

a gripping portion at which the manual release mechanism is disposed; and a front handle portion extending from an end portion of the gripping portion and connected to the operating console, the wire extending out of the manual release mechanism extending along and through the front handle portion.

5. The medical apparatus according to claim 1, wherein, the manual release mechanism is disposed at the operating console.

6. The medical apparatus according to claim 1, wherein, the limiting mechanism comprises at least one of a lifting limiting mechanism and a rotating limiting mechanism, and in the case where the pressing force is applied to the manual release mechanism, the limiting mechanism releases the limitation on lifting and/or the movement of the operating console.

7. The medical apparatus according to claim 1, wherein, the first guide portion is a protruding portion, the second guide portion is a recessed portion, and extension directions of the protruding portion and the recessed portion are parallel to the direction of the pressing force, or the first guide portion is a recessed portion, the second guide portion is a protruding portion, and extending directions of the protruding portion and the recessed portion are parallel to the direction of the pressing force.

8. The medical apparatus according to claim 1, wherein, the medical apparatus comprises at least one of an ultrasound imaging apparatus, an electrocardiograph, and a monitor.

9. The medical apparatus according to claim 1, wherein, the wire is capable of transmitting a pulling force, and the conversion portion converts the pressing force into a stretching force on the wire; or, the wire is capable of transmitting a pushing force, and the conversion portion converts the pressing force into a pushing force on the wire.

10. The medical apparatus according to claim 1, wherein, the medical apparatus comprises a gripping mechanism, comprising:

a gripping portion at which the manual release mechanism is disposed; and a front handle portion extending from an end portion of the gripping portion and connected to the operating console, the wire extending out of the manual release mechanism extending along and through the front handle portion.

11. The medical apparatus according to claim 1, wherein, the manual release mechanism is disposed at the operating console.

12. The medical apparatus according to claim 1, wherein, the limiting mechanism comprises at least one of a lifting limiting mechanism and a rotating limiting mechanism, and in the case where the pressing force is applied to the manual release mechanism, the limiting mechanism releases the limitation on lifting and/or the movement of the operating console.

13. The medical apparatus according to claim 1, wherein, the first guide portion is a protruding portion, the second guide portion is a recessed portion, and extension directions of the protruding portion and the recessed portion are parallel to the direction of the pressing force, or the first guide portion is a recessed portion, the second guide portion is a protruding portion, and extending directions of the protruding portion and the recessed portion are parallel to the direction of the pressing force.

14. A medical apparatus, comprising:

an operating console of the medical apparatus;

a limiting mechanism connected to the operating console, the limiting mechanism being capable of limiting movement of the operating console; and a manual release mechanism connected to the limiting mechanism through a wire, the limiting mechanism releasing the limitation on the movement of the operating console based on a pressing force being applied to the manual release mechanism, and the manual release mechanism comprising:

a handle receiving the pressing force;

a conversion portion connected to the handle and converting the pressing force into an acting force on the wire, a direction of the acting force intersecting a direction of the pressing force; and a base portion on which the handle and the conversion portion are mounted, wherein the handle is provided with a first guide portion, the base portion is provided with a second guide portion that cooperates with the first guide portion, and in a case where the pressing force is applied to the handle, the handle moves linearly in a direction perpendicular to the base portion under guidance of the first guide portion and the second guide portion, wherein a lever is connected to the end of the wire away from the manual release mechanism, the lever is connected to the limiting mechanism, and the limiting mechanism is driven by the lever to release the limitation on the movement of the operating console, wherein a stroke of the wire is greater than a stroke of the handle, and wherein, the conversion portion comprises:

a first idle wheel disposed at the handle, and a second idle wheel disposed at the base portion, the second idle wheel and the first idle wheel being disposed at different positions in an extension direction of the wire, the wire being disposed between the first idle wheel and the second idle wheel, an end portion of the wire being fixed to the base portion, and the first idle wheel and the second idle wheel pressing the wire in the case where the pressing force is applied to the handle.

15. The medical apparatus according to claim 14, wherein, the number of the first idle wheels is two, the number of the second idle wheels is two, the two first idle wheels and the two second idle wheels are sequentially arranged at intervals, and the end portion of the wire fixed to the base portion is close to one of the two first idle wheels.

16. A medical apparatus, comprising:

an operating console of the medical apparatus;

a limiting mechanism connected to the operating console, the limiting mechanism being capable of limiting movement of the operating console; and a manual release mechanism connected to the limiting mechanism through a wire, the limiting mechanism releasing the limitation on the movement of the operating console based on a pressing force being applied to the manual release mechanism, and the manual release mechanism comprising:

a handle receiving the pressing force;

a conversion portion connected to the handle and converting the pressing force into an acting force on the wire, a direction of the acting force intersecting a direction of the pressing force; and a base portion on which the handle and the conversion portion are mounted, wherein the handle is provided with a first guide portion, the base portion is provided with a second guide portion that cooperates with the first guide portion, and in a case where the pressing force is applied to the handle, the handle moves linearly in a direction perpendicular to the base portion under guidance of the first guide portion and the second guide portion, wherein a lever is connected to the end of the wire away from the manual release mechanism, the lever is connected to the limiting mechanism, and the limiting mechanism is driven by the lever to release the limitation on the movement of the operating console, wherein a stroke of the wire is greater than a stroke of the handle, and wherein, the conversion portion comprises:

a rack disposed at the handle, and a gear disposed at the base portion and capable of being driven by the rack to rotate, the wire being fixed to the gear.

17. The medical apparatus according to claim 16, wherein, an outer peripheral portion of the gear comprises a toothed portion that meshes with the rack, and an extension portion to which the wire is fixed, and a distance of a fixed position of the wire from a rotation center of the gear is greater than a distance of the toothed portion of the gear from the rotation center.

* * * * *